United States Patent [19]
Baker et al.

[11] Patent Number: 4,685,423
[45] Date of Patent: Aug. 11, 1987

[54] INSECTICIDAL GROOMING ARTICLE

[75] Inventors: Rodney C. Baker, Leighton Buzzard, England; Phillippus J. Van Rensburg, Randburg, South Africa

[73] Assignee: AECI Limited, Johannesburg, South Africa

[21] Appl. No.: 787,138

[22] Filed: Oct. 15, 1985

Related U.S. Application Data

[63] Continuation-in-part of Ser. No. 594,531, Mar. 29, 1984, Pat. No. 4,604,971.

[30] Foreign Application Priority Data

Apr. 13, 1983 [ZA] South Africa .................... 83/2597

[51] Int. Cl.$^4$ ............................................ A01K 13/00
[52] U.S. Cl. ...................................... 119/86; 119/156; 15/104.93
[58] Field of Search .................. 119/83, 86, 93, 156, 119/157; 132/142; 15/104.93, 104.94

[56] References Cited

U.S. PATENT DOCUMENTS

| | | | |
|---|---|---|---|
| 3,496,589 | 2/1970 | Demner | 15/104.93 |
| 4,143,982 | 3/1979 | Cox et al. | 401/280 |
| 4,213,423 | 7/1980 | Bryan et al. | 119/86 |
| 4,237,822 | 12/1980 | Kaiser, Jr. | 119/85 |
| 4,250,838 | 2/1981 | Ott | 119/156 X |

FOREIGN PATENT DOCUMENTS

| | | | |
|---|---|---|---|
| 248726 | 12/1963 | Australia | 15/104.93 |
| 2372623 | 6/1978 | France . | |

*Primary Examiner*—Robert P. Swiatek
*Attorney, Agent, or Firm*—Cushman, Darby & Cushman

[57] ABSTRACT

The invention provides an article for grooming an animal and comprising a grooming article of plastics material, the plastics material containing, over at least a portion thereof, at least one insecticide capable of blooming from the article onto the animal when the article is used. The article may be a brush or comb. If desired, only a portion thereof may contain insecticide.

3 Claims, 4 Drawing Figures

INSECTICIDAL GROOMING ARTICLE

This is a continuation in part of Ser. No. 594,531, filed Mar. 29, 1984, now U.S. Pat. No. 4,604,971.

This invention relates to an insecticidal grooming article.

The present invention provides an article for grooming an animal and comprising a grooming article of moulded plastics material, said plastics material containing, over at least a portion thereof, at least one insecticide capable of blooming from the article onto an animal when the article is used.

The grooming article conveniently is in the shape of a brush or comb. If desired, only some of the bristles of the brush, or teeth of the comb, may contain insecticide, and the remainder may be insecticide-free. In the case of a brush, there may be soft bristles containing the insecticide, and stiff bristles for assisting in the grooming. The different bristles may be in different areas. Alternatively, all the bristles of the brush or teeth of the comb may be of insecticidally-containing plastics material.

If desired, the grooming article may include a replaceable portion containing the insecticide. For example, a middle portion of a brush may be replaceable while the surrounding portions may have bristles which are insecticide-free.

The insecticidal material must be capable of blooming sufficiently to have an insecticidal effect when the article is used to groom an animal, particularly a household animal such as a dog or cat. The insecticide blooms out of the article along the bristles, teeth, or the like, of the brush, comb, or the like.

There may be a single insecticide or a plurality of insecticides. If desired, when there is more than one insecticide, different areas of the grooming article can contain different insecticides This can overcome or reduce problems of chemical incompatibility of insecticides.

The invention also provides a method of manufacturing a grooming article, which comprises moulding a grooming article from a plastics composition comprising a plastics material and at least one insecticide capable of blooming out of the article, in use.

Conveniently, the composition may also contain a plasticizer as well as other agents which affect the speed with which the insecticide blooms from the article and/or compounds for enabling the insecticide to be retained in the plastics material during moulding. Thus, extenders, fillers, or the like, can be present.

The composition may contain from 10 to 50% (by mass), preferably from 20 to 30% (by mass), plasticizer, and from 5 to 40% (by mass), preferably 10 to 25% (by mass), insecticide.

The insecticide may be any one or more of:
amitraz, (i.e. N,N-di-(2,4-xylyliminomethyl) methylamine);
lindane, (i.e. 1,2,3,4,5,6-hexachlorocyclohexane);
diazinon, (i.e. O,O-diethyl-O-2-isopropyl-6-methyl pyrimidin-4-ylphosphorothioate);
dichlorvos, (i.e. 2,2-dichlorovinyl dimethyl phosphate);
propoxur, (i.e. 2-isopropoxyphenyl methylcarbamate);
tetrachlorvinphos, (i.e. 2-chloro-1-(2,4,5-trichlorophenyl) vinyl dimethyl phosphate);
dursban, (i.e. O,O-diethyl-O-3,5,6-trichloro-2-pyridyl-phosphorothioate);
carbaryl, (i.e. 1-naphthalenyl methyl carbamate);
trichlorphon, (i.e. 2,2,2-trichloro-1-hydroxyethylphosphonate);
phosmet, (i.e. O,O-dimethyl S-phthalimidomethyl phosphorodithioate) which may be recrystallized to remove or reduce its offensive odour; or a synthetic pyrethroid optionally admixed with a synergist, such as piperonyl butoxide.

Synthetic pyrethroids include:
permethrin (i.e. 3-phenoxybenzyl-($\pm$)-cis, trans-2,2-dimethyl-3-(2,2-dichlorovinyl) cyclopropane-1-carboxylate);
deltamethrin (i.e. S-$\alpha$-cyano-3-phenoxy benzyl-(1R,3R)2,2-dimethyl-3-(2,2-dibromovinyl) cyclopropane-1 carboxylate); and
tetramethrin (i.e. 3,4,5,6-tetrahydro-phthalimidomethyl($\pm$)cis,trans-chrysanthemate).

The amount of insecticide present may vary, depending on the insecticide, the plastics material, and the other constituents present.

The grooming article provided by the invention can be used for the control of ticks, fleas, or other insects on non- human animals.

Any suitable plastics material may be used. The plastics material may comprise one or more of polyethylene, polypropylene, polyvinylchloride, nylon, nitrile rubbers, ethyl vinyl acetate polymers, and the like. Any suitable method of manufacture may be used, for example injection-moulding.

In addition to the plastics material and the insecticide, plasticisers, extenders, fillers, lubricants, stabilizers, and the like, can be present. The stabilizers may for example be heat stabilizers, such as TBLS, or stabilizers such as calcium oxide, epoxidised soya bean oil, or other suitable epoxy compounds, for one or more of the insecticides. Lubricants can include stearic acid. The plasticiser may, for example, be di-isooctyl adipate. If desired, odour maskers (e.g. perfumes), or odour absorbers, to overcome unpleasant insecticide smells, may be included.

Examples of extenders are chlorinated hydrocarbons, such as those available under the trade names Cereclor, Conoflex, Mobilsol and Mesamoll, expoxidised soyabean oil, and the like.

Examples of fillers are talc, silica, diatomaceous earth, china clay, and the like.

Although soft plastics materials such as polyethylene and polyvinylchloride can be used, nylon may also be considered. The grooming article must be sufficiently hard to be used without breaking. Since it is normally in the form of a brush or comb, this determines to a large extent the hardness of the plastics material used. It must be flexible but not brittle, and must allow blooming of the insecticide from the article.

If desired, other materials can be used in addition for some of the teeth or bristles, e.g. steel, animal hair, or the like.

The invention is illustrated in non-limiting manner by reference to the following Examples of compositions which can be used to prepare brushes according to the invention by plastics moulding.

EXAMPLES 1 to 4

| Constituent | Ex. 1 | Ex. 2 | Ex. 3 | Ex. 4 |
| --- | --- | --- | --- | --- |
| Amitraz | 15.0 | 15.0 | 15.0 | 15.0 |
| Lindane | 15.0 | 15.0 | 15.0 | 15.0 |

-continued

| Constituent | Ex. 1 | Ex. 2 | Ex. 3 | Ex. 4 |
| --- | --- | --- | --- | --- |
| Polyethylene (linear low density) 7042 | 25.0 | 39.5 | 36.5 | 31.5 |
| PVC (Corvic S6611) | 39.5 | 25.0 | 19.8 | 14.8 |
| Heat Stabilizer (TBLS) | 3.0 | 3.0 | 3.0 | 3.0 |
| Calcium oxide stabilizer | 2.5 | 2.5 | 2.5 | 2.5 |
| Nitrile rubber NS | — | — | 8.0 | 8.0 |
| Stearic acid lubricant | — | — | 0.2 | 0.2 |
| Di-isooctyl adipate plasticizer | — | — | — | 10.0 |

The amounts given above and also hereinafter are percentages by weight or mass. The constituents were melted together and the molten mass was extruded to form a brush. The brush obtained was suitable for brushing dogs and the like to remove ticks, fleas, etc.

The invention is illustrated by reference to the accompanying drawings, in which FIG. 1 is a plan view of the underside of brush according to one embodiment of the invention;

Figure 1:
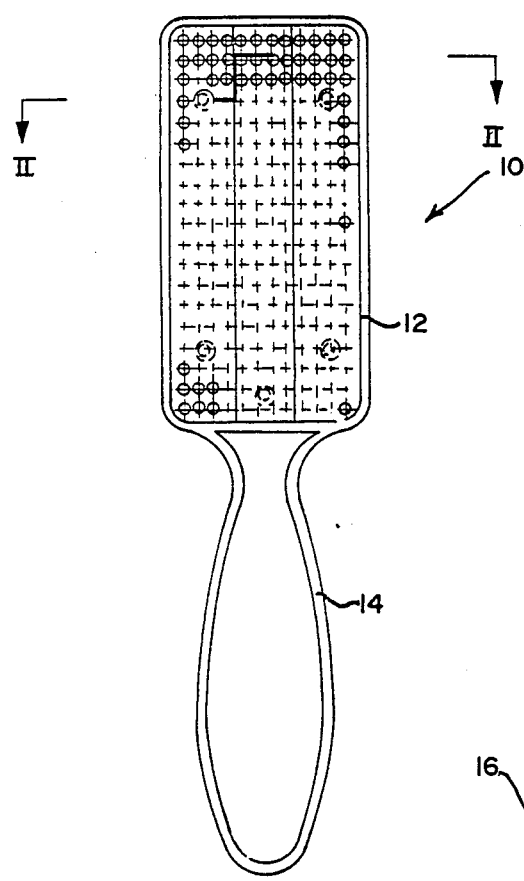
Figure 2:
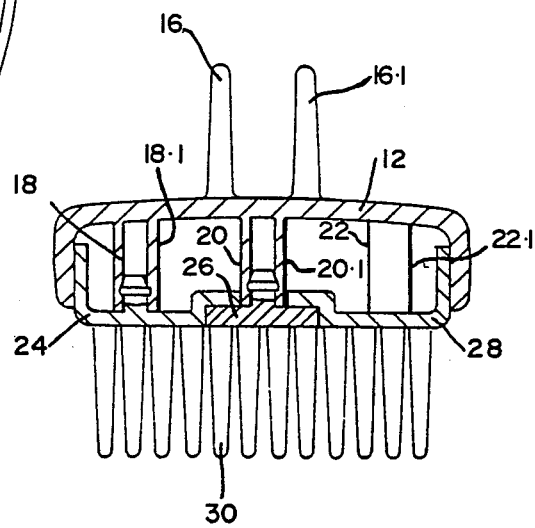
FIG. 2 is a section along II—II of FIG. 1.

In FIGS. 1 and 2, a brush shown generally at 10, has a head 12 and a handle 14.

The head 12 has rows of bristles 16, 16.1 extending from its upper surface and gripping channels 18, 18.1, 20, 20.1 and 22, 22.1 extending from its lower surface. Bristle holders 24, 26, 28 fit in tight frictional grip in the channels 18, 18.1, 20, 20.1 and 22, 22.1.

The central bristle holder 26 has bristles 30 and is moulded from a plastics mixture comprising a plastics material and an insecticide capable of blooming out therefrom.

The outer bristle holders 24 and 28 are also of plastics material but are free from insecticide. The central bristle holder 26 is replaceable.

Figure 3:
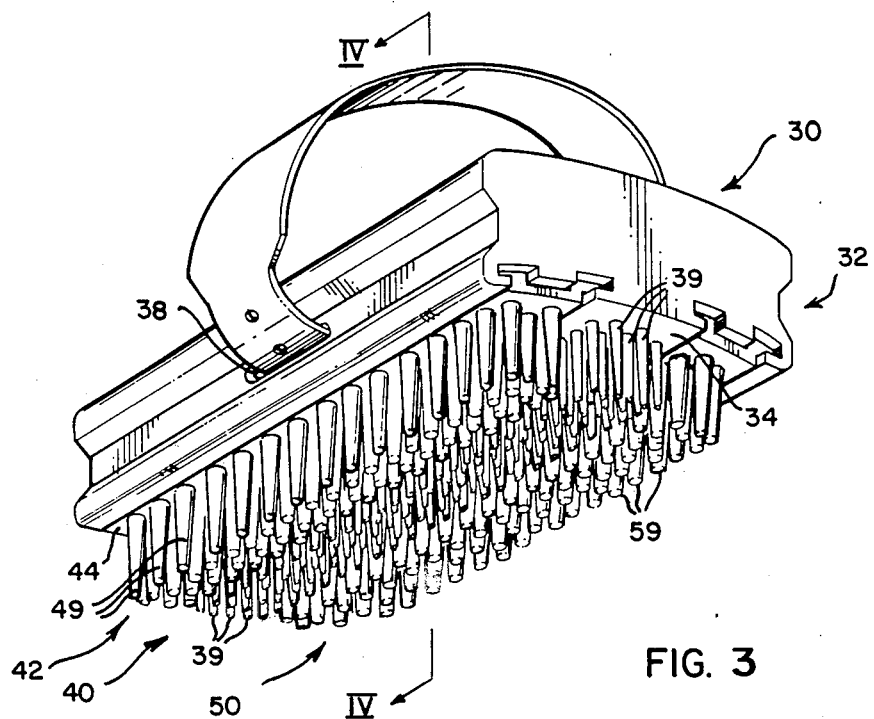
FIG. 3 is a three dimensional view from the bottom of a brush according to another embodiment of the invention.
Figure 4:
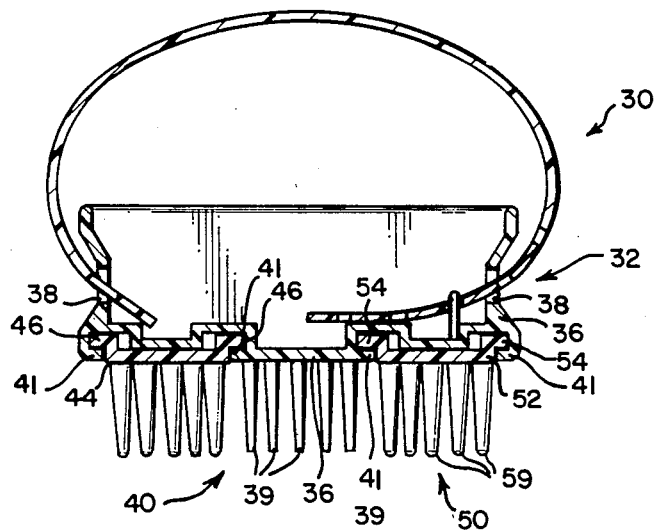
FIG. 4 is a sectional view through IV—IV in FIG. 3.

In FIGS. 3 and 4, reference numeral 30 generally indicates a brush according to another embodiment of the invention.

The brush 30 includes a hand grippable portion 32 which is U-shaped in cross section. It has a base 34 and upstanding sides 36. In two opposed sides there are provided apertures 38 through which, in use, a securing strap (not shown) for securing the portion 32 to a user's hand (not shown) can pass.

The brush 30 includes, along a central portion of the base 34 and protruding from its underside, a plurality of bristles 39 of plastics material, arranged in 5 rows to form a core 40. The plastics material may be polypropylene.

The portion 32 and the bristles of the core 40 are an integral unit i.e. are moulded together, and the bristles 39 are relatively hard so that, in use, they will perform a grooming function. The bristles 39 are of substantially constant diameter along their lengths; their diameter is a 1-2 mm; their length is about 1.5 cm; they are arranged in 5 rows each containing about 40 bristles and the bristles of the one row are staggered w.r.t. those at an adjacent row.

The brush 30 also includes a first insert 42 comprising a base 44, tongues 46 along the base which engage complementary grooves defined by flanges 41 on the portion 32 thereby to secure the insert releasably to the underside of the base 34, and 72 bristles 49. The bristles 49 comprise plastics material, such as polyvinyl chloride, containing a first insecticide. The bristles 49 are arranged in 5 spaced rows.

The brush 30 further includes a second insert 50 also comprising a base 52, tongues 54 along the base which releasably engage complementary grooves defines by flanges 41 on the portion 32, and 72 bristles 59. The bristles 59 comprise plastics material containing a second insecticide which is different to the first insecticide.

The bristles 49, 50 taper downwardly from the base 44, 52 respectively to their tips from a diameter of about 4mm to a diameter of about 2 mm. The bristles in adjacent rows arm staggered longitudinally so that the spacing between adjacent teeth (at their tips) is about 0.5 cm.

The insecticide of the bristles 49 may be effective against fleas, and may comprise dursban. The bristles 49 may comprise polyvinylchloride containing about 30% deodorized techinical dursban. In particular, the bristles 49 may comprise

| | |
| --- | --- |
| Dursban "R" (low odour chlorpyrifos) | 28,8% |
| Diisooctyl Adipate | 25,0% |
| "Corvic' S 6617 (polyvinylchloride manufactured by AECI) | 42,0% |
| 'Interstab' M103 ZF (barium cadmium heat stabilizer manufactured by Chemserve Technical Products) | 1,6% |
| Stearic Acid | 0,2% |
| 'Reoplast' 39 (expoxidised soya bean oil) | 2,0% |
| Butylated Hydroxytoluene | 0,2% |
| 'Vynamon' red 2G (red pigment manufactured by ICI) | 0,2% |

The insecticide of the bristles 59 may be effective against ticks, and may comprise amitraz. The bristles 59 may comprise plastics material and about 25% technical amitraz. In particular, the bristles 59 may comprise:

| | |
| --- | --- |
| Amitraz, tech (95% pure) | 26,3% |
| Diisooctyl Adipate | 25,0% |
| 'Corvic' S 6617 | 41,9% |
| 'Interstab' M103 ZF | 1,6% |
| Stearic Acid | 0,2% |
| Calcium Oxide | 5,0% |

In another embodiment, the bristles 59 may comprise:

| | |
| --- | --- |
| Phosmet Recrystallised (95% pure) | 30,8% |
| Diisooctyl Adipate | 25,0% |
| 'Corvic' S 6617 | 42,4% |
| 'Interstab' M103 ZF | 1,6% |
| Stearic Acid | 0,2% |

The polyvinylchloride bristles 49, 59 are softer, i.e. are more flexible, than the polypropylene bristles 39.

A brush 30 having bristles 49 containing about 30% dursban and bristles 59 containing about 25% amitraz was manufactured by injection moulding. It was then stored for six months at ambient temperature following manufacture thereof. Tests were conducted with the brush by stroking towels of about 1 ft by 0.5 ft with sets of 30 strokes at a time, each set of 30 strokes being followed immediately by the next set of 30 strokes, and each set of strokes being applied to a fresh towel. These tests were based on the assumption that about 30 strokes are required to brush or groom a medium-sized dog thoroughly i.e. to stroke all portions of its coat or pelt three times, and that 30 strokes take about 10 minutes to apply. Each towel was then analysed for insecticidal deposit, and the following results obtained:

TABLE I

| Cumulative No. strokes | Dursban (mg) on Towel | Blooming rate$^x$ mg/time unit | Amitraz (mg) on Towel | Blooming rate$^x$ mg/time unit |
| --- | --- | --- | --- | --- |
| 30 | 6,91 | 0.0003$^{xx}$ | 12.6 | 0.0005$^{xx}$ |
| 60 | 1,29 | 1,29 | 5,9 | 5,9 |
| 90 | 0,95 | 0,95 | 5,3 | 5,3 |
| 120 | 0,80 | 0,80 | 3,6 | 3,6 |
| 150 | 0,58 | 0,58 | 2,4 | 2,4 |
| 180 | 0,61 | 0,61 | 2,2 | 2,2 |
| 210 | 0,72 | 0,72 | 2,7 | 2,7 |
| 240 | 0,57 | 0,57 | 2,5 | 2,5 |
| 270 | 0,53 | 0,53 | 3,1 | 3,1 |
| 300 | 0.65 | 0,65 | 2,4 | 2,4 |

$^x$time unit of 10 minutes
$^{xx}$calculated on storage time of 6 months i.e. 26208 time units of ten minutes The brush was then stored, unused, for three days whereafter the tests were repeated, giving the following results:

TABLE II

| Cumualte No. of strokes | Dursban (mg) | Blooming rate$^{xxx}$ mg/time unit | Amitraz (mg) | Blooming rate$^{xxx}$ mg/time unit |
| --- | --- | --- | --- | --- |
| 30 | 0,60 | 0,001$^{xxxx}$ | 10,1 | 0,023$^{xxxx}$ |
| 60 | 0,46 | 0,46 | 6.6 | 6,6 |
| 90 | 0,35 | 0,35 | 4,8 | 4,8 |
| 120 | 0,36 | 0,36 | 2,6 | 2,6 |
| 150 | 0,37 | 0.37 | 1,9 | 1,9 |
| 180 | 0,43 | 0,43 | 2,1 | 2,1 |
| 210 | 0,30 | 0,30 | 1,3 | 1,3 |
| 240 | 0,35 | 0,35 | 1,0 | 1,0 |
| 270 | 0,41 | 0,41 | 1,0 | 1,0 |
| 300 | 0,36 | 0,36 | 1,2 | 1,2 |

$^{xxx}$time unit at 10 minutes
$^{xxxx}$calculated on storage time of 5 minutes i.e. 432 time units of 10 minutes These tests show that a consistent and sufficient amount of insecticide blooms from the bristles per unit time during grooming, even during successive grooming cycles.

Furthermore, when not in use, only a relatively small amount of insecticide per unit time, i.e. which is lower than that which blooms out during grooming, blooms out. This is evident from the first row of readings in the tables above.

Hence, the insecticide is capable of blooming out continuously from the bristles during use, in an insecticidally effective amount. Still further, when not in use, the insecticide does not bloom out to the same extent. In other words, the rate of blooming out is greater when the brush is being used to groom an animal, i.e. when the bristles are being flexed, than is the case when the article is not in use, e.g. when it is being stored. Apart from reducing insecticide wastage, this feature is also a safety feature since only a relatively small amount of insecticide, which could be hazardous to a person inadvertently touching the brush blooms out and accumulates on the outer surface of the bristles when it is not in use.

The Applicant is also aware of insecticidal collars for animals. These collars are of plastics material impregnated with an insecticide such as propoxur, and diazenon. However, the mechanism by which these collars work is the sustained or continuous release of relatively minute doses of insecticide for the duration of the life of the collar to obtain satisfactory insecticidal control on animals. For example, Dick et al (U.S. Pat. No. 4,150,109) teaches a collar having a life of 6 months (Col 6 1 L 29–35) and 19 weeks (Col 15 lines 38 and 59). In contrast, with the grooming article provided by the present invention good insecticidal control is obtained for long periods by the release of sufficient insecticide onto the animal over a very short period while grooming e.g. 10 minutes. This is borne out by the following tests which were conducted:

Brush A having a central core comprising 5 rows each containing 35 bristles spaced 4 mm apart, was used. A bristled section adjoined the core on either side thereof and comprised insecticide-containing bristles. Each bristled section comprised 3 rows each containing 21 bristles. The bristles of these sections were spaced 6 mm apart, and each bristled section had a mass of 19.2 g. Hence, the bristled sections provided a total of 126 insecticide-containing bristles. The widths of the brishes were 75 mm, and their lenghs 136 mm.

The insecticide-containing bristles of Brush A were moulded from a composition which comprised the following:

| | |
| --- | --- |
| Amitraz technical (95% pure) | 15.8% (by mass) (equivalent to 15.0% Amitraz) |
| PVC (Corvic S6611) | 52.4 (by mass) |
| heat stabilizer (INTERSTAB M103 ZF) | 1.6 (by mass) |
| calcium oxided stabilizer | 5.0 (by mass) |
| stearic acid lubricant | 0.2 (by mass) |
| di-isooctyl adipate plasticizer | 25.0 (by mass) |

Biological tests were then conducted with this brush as follows:

On day 1, Dog A was challenged with 20 R.Sanguineus and 20 H.Leachi adult ticks;

On day 8 the dog was again challenged with the same number of each species of ticks;

On day 15, a tick count was done on the dogs. Dog A was found to have a total of 54 ticks comprising 37 male and female R.Sanguineus and 17 male and feamle H.Leachi ticks.

On day 16, the dog was again challenged with 20 R.Sanguineus and 20 H.Leachi adult ticks.

On day 18, a tick count was done on the dog. Dag A was found to have 67 ticks comprising 42 R.Sanguineus male and female ticks and 25 H.Leachi male and female ticks. Immediately after this count, Day A was treated by brushing it with Brush A. The entire haircoat of the animal was firmly brushed three times, the total duration of the brushing being about 10 minutes for the animal.

On day 19, a tick count was again done. No ticks were found on Dog A.

On Day 23, a tick count was again done. No ticks were found on Dog A. Immediately thereafter the dog was again treated by brushing it as hereinbefore described. After this treatment, the dog was again challenged, on Day 23, with 20 R.Sanguineus and 20 H. Leachi adult ticks.

On Day 25, a tick count was again done. No ticks were found on Dog A. Immediately after this tick count, the dog was again treated by brushing it as hereinbefore described.

On Day 29, a tick count was again done. Not ticks were found on Dog A. Immediately after this tick count, the dog was yet again treated by brushing it as hereinbefore described.

Yet further tests were then conducted with a brush 30 as hereinbefore described, i.e. having amitraz and dursban containing bristles, to show it being effective agaist ticks and fleas and with a commercially available insecticidal collar containing 9.4% propoxur impregnated plastics material. The results as set out in table III and IV were obtained

TABLE III

FLEA COUNTS ON DOGS TREATED WITH BRUSHES CONTAINING DURSBAN 30% AND AMITRAZ 25% IMPREGNATED SETS OF BRISTLES AND WEARING A COMMERCIALLY AVAILABLE COLLAR IMPREGNATED WITH 9.4% PROPOXUR

| DAY | DURSBAN/AMITRAZ BRUSHES | | | | | | | | | COLLAR | | |
|---|---|---|---|---|---|---|---|---|---|---|---|---|
| | 229 | 156 | 233 | 139 | 158 | 179 | 157 | 138 | AV | 220 | 151 | AV |
| −8* | | | | | | | | | | | | |
| −7 | 57 | 52 | 70 | 46 | 58 | 37 | 39 | 38 | 50 | 46 | 35 | 41 |
| −1* | | | | | | | | | | | | |
| 0** | 61 | 45 | 78 | 57 | 58 | 60 | 59 | 75 | 62 | 70 | 63 | 62 |
| 1** | 20 | 5 | 21 | 4 | 5 | 19 | 7 | 3 | 11 | 0 | 6 | 3 |
| 5** | 1 | 0 | 0 | 0 | 0 | 1 | 1 | 0 | 0 | 0 | 1 | 1 |
| 6** | | | | | | | | | | | | |
| 8** | 1 | 0 | 0 | 0 | 0 | 2 | 0 | 0 | 0 | 0 | 0 | 0 |
| 12** | 0 | 0 | 0 | 0 | 0 | 0 | 0 | 0 | 0 | 0 | 0 | 0 |
| 13* | | | | | | | | | | | | |
| 15** | 2 | 0 | 1 | 0 | 0 | 0 | 0 | 1 | 1 | 5 | 0 | 3 |
| 19** | 0 | 0 | 0 | 0 | 0 | 0 | 0 | 0 | 0 | 3 | 0 | 2 |
| 20* | | | | | | | | | | | | |
| 22** | 0 | 0 | 0 | 0 | 1 | 1 | 0 | 0 | 0 | 19 | 4 | 12 |
| 26** | 0 | 0 | 0 | 0 | 0 | 2 | 0 | 0 | 0 | 12 | 2 | 7 |
| 27* | | | | | | | | | | | | |
| 29** | 2 | 1 | 0 | 0 | 0 | 0 | 0 | 0 | 1 | 25 | 7 | 10 |
| 33** | 0 | 0 | 0 | 0 | 0 | 0 | 0 | 0 | 0 | 16 | 4 | 10 |
| 34* | | | | | | | | | | | | |
| 35** | 4 | 1 | 5 | 1 | 1 | 5 | 9 | 3 | 4 | 22 | 16 | 19 |
| 40** | 0 | 0 | 0 | 0 | 0 | 3 | 0 | 0 | 0 | 16 | 8 | 12 |
| 41* | | | | | | | | | | | | |
| 42 | 1 | 1 | 5 | 1 | 1 | 13 | 2 | 3 | 4 | NC | NC | |
| 43** | 1 | 1 | 0 | 1 | 0 | 6 | 2 | 3 | 2 | 25 | 12 | 19 |
| 44 | | | | | 0 | 3 | 0 | 1 | 1 | | | |
| 47** | | | | | 0 | 1 | 0 | 0 | 0 | | | |
| 48* | | | | | | | | | | | | |
| 49 | | | | | 4 | 20 | 1 | 4 | 7 | | | |
| 50** | | | | | 1 | 11 | 0 | 2 | 4 | | | |
| 54** | | | | | 0 | 4 | 0 | 0 | 1 | | | |
| 55* | | | | | | | | | | | | |
| 56 | | | | | 0 | 19 | 1 | 2 | 6 | | | |
| 57** | | | | | 0 | 12 | 1 | 1 | 4 | | | |
| 58 | | | | | 0 | 11 | 0 | 0 | 3 | | | |

Legend:
x: Tick challenge comprising 20 unfed adult *Haemaphysalis leachi* ticks 20 unfed adult *Rhipicephalus sanguineus* ticks and 100 freshly emerged adult *Ctenocephalides felis* fleas.
xx: Treatment/Collar attachment Day 0
AV: Average
NC: No count
Note: Dogs 157 and 138 treated, in the order given, using the same brush; dogs 229, 156, 233, 139, 158, and 189 treated with separate individually identified brushes On day 15 Dog 220's collar not blooming, Dog 151's collar still blooming. (Stopped blooming around Day 22)

TABLE IV

TICK COUNTS ON DOGS TREATED WITH BRUSHES CONTAINING DURSBAN 30% AND AMITRAZ 25% IMPREGNATED SETS OF BRISTLES AND WEARING A COMMERCIALLY AVAILABLE COLLAR IMPREGNATED WITH 9.4% PROPOXUR

| DAY | DURSBAN/AMITRAZ BRUSHES | | | | | | | | | COLLAR | | |
|---|---|---|---|---|---|---|---|---|---|---|---|---|
| | 229 | 156 | 233 | 139 | 158 | 179 | 157 | 138 | AV | 220 | 151 | AV |
| −8* | | | | | | | | | | | | |
| −7 | 20(20) | 21(14) | 14(17) | 9(18) | 15(12) | 14(10) | 8(12) | 14(16) | 30 | 23(12) | 11(5) | 26 |
| −1* | | | | | | | | | | | | |
| 0** | 29(22) | 18(18) | 24(23) | 19(24) | 20(10) | 20(23) | 22(17) | 21(18) | 41 | 38(20) | 13(15) | 43 |
| 1** | 3(4) | 2(5) | 6(6) | 0(10) | 2(1) | 9(10) | 6(8) | 7(9) | 11 | 7(2) | 0(5) | 7 |
| 5** | 0 | 0 | 0(1) | 0 | 0 | 2(1) | 0 | 0(3) | 1 | 0 | 0 | 0 |
| 6* | | | | | | | | | | | | |
| 8** | 0 | 1(0) | 0(2) | 0 | 0 | 1(2) | 0 | 1(0) | 1 | 0(1) | 0 | 1 |
| 12** | 0 | 1(0) | 0(1) | 0 | 0 | 0 | 0 | 0 | 0 | 0 | 0 | 0 |
| 13* | | | | | | | | | | | | |
| 15** | 0 | 0 | 0 | 0 | 0 | 0 | 0 | 0 | 0 | 6(2) | 0 | 4 |
| 19** | 0 | 0 | 0 | 0 | 0 | 0 | 0 | 0 | 0 | 2(1) | 0 | 2 |
| 20* | | | | | | | | | | | | |
| 22** | 0 | 0 | 0 | 0 | 0 | 0(1) | 0 | 0 | 0 | 7(4) | 0 | 6 |
| 26** | 0 | 0 | 0 | 0 | 0 | 0(1) | 0 | 0 | 0 | 4(4) | 0 | 4 |
| 27* | | | | | | | | | | | | |
| 29** | 0 | 0 | 0 | 0 | 0 | 0 | 0 | 0 | 0 | 10(12) | 0 | 11 |
| 33** | 0 | 0 | 0 | 0 | 0 | 0 | 0 | 0 | 0 | 12(6) | 0 | 9 |
| 34* | | | | | | | | | | | | |
| 35** | 0 | 1(0) | 0 | 0 | 0 | 0(2) | 0 | 0 | 1 | 14(23) | 0 | 14 |

TABLE IV-continued
TICK COUNTS ON DOGS TREATED WITH BRUSHES CONTAINING DURSBAN 30% AND AMITRAZ 25% IMPREGNATED SETS OF BRISTLES AND WEARING A COMMERCIALLY AVAILABLE COLLAR IMPREGNATED WITH 9.4% PROPOXUR

| DAY | DURSBAN/AMITRAZ BRUSHES | | | | | | | | | COLLAR | | |
|---|---|---|---|---|---|---|---|---|---|---|---|---|
| | 229 | 156 | 233 | 139 | 158 | 179 | 157 | 138 | AV | 220 | 151 | AV |
| 40** | 0 | 1(0) | 0 | 0 | 0 | 0(1) | 0 | 0 | 0 | 8(13) | 0 | 11 |
| 41* | | | | | | | | | | | | |
| 42 | 0 | 0 | 0 | 0 | 0 | 0(1) | 0 | 0 | 0 | NC | NC | |
| 43** | 0 | 0 | 0 | 0 | 0 | 0(1) | 0 | 0 | 0 | 11(23) | 1(1) | 18 |
| 44 | | | | | 0 | 0(1) | 0 | 0 | 0 | | | |
| 47** | | | | | 0 | 0 | 0 | 0 | 0 | | | |
| 48* | | | | | | | | | | | | |
| 49 | | | | | 1(0) | 0 | 0 | 0 | 0 | | | |
| 50** | | | | | 0 | 0 | 0 | 0 | 0 | | | |
| 54** | | | | | 0 | 0 | 0 | 0 | 0 | | | |
| 55* | | | | | | | | | | | | |
| 56 | | | | | | 1(1) | 0 | 0 | .5 | | | |
| 57** | | | | | | 0(2) | 0 | 0 | .5 | | | |
| 58 | | | | | | 0 | 0 | 0 | 0 | | | |

Legend:
x: Tick challenge (as for table III)
xx: Treatment/Collar attachment Day 0
AV: Average
NC: No count
a(b): a represents *Haemaphysalis leachi* ticks b represents *Rhipicephalus sanguineus* ticks
Note: Dogs 157 and 138 treated, in the order given, using the same brush: On Day 15 Dog 220's collar not blooming, Dog 151's collar still blooming. (Stopped blooming around Day 22)

In these tests the treatments with the brushes were effected on two consecutive days initially, followed thereafter by twice weekly treatment. Each treatment comprised firmly brushing the entire hair coat of the medium sized dogs (Beagles) three times. Each treatment of a dog took about 10 minutes.

As can be seen in the tables good control of ticks was being achieved by day 5 with the brush treated dogs as well as the collared dogs. However, in the case of the collared dogs this control commenced deteriorating around day 29; good tick control was maintained with the brushed dogs up to day 58 when the tests were terminated.

Good flea control was obtained with the brushed dogs by day 5 as was the case with the collared dogs. The control in respect of the collared dogs deteriorated around day 22, while good control with the brushed dogs was maintained up to day 58.

From the results obtained with brushed dogs 157 and 138 it can be concluded that the efficiency of the brush according to the present invention is not reduced when two medium sized dogs are consecutively brushed twice weekly for an extended period of up to 8 weeks or longer, with one brush.

Analyses were effected on the used brushes (used in the tests of tables III and IV as well as unused similar brushes, and it was determined that about 5.7% of the total dursban and about 15.4% of the total amitraz bloomed from the bristles of the brushes during the tests.

None of the brushed dogs showed any evidence of skin irritation or systemic toxicity during the tests.

Hence, with the brush 30, good insecticidal control is obtained in spite of relatively low dosage rates, which is advantageous e.g. low dosage rates are cost effective as the brush lasts for a long time. Furthermore, as mentioned, the brush has a differential rate of blooming when in use and when not in use which also leads to insecticide savings as well as being a safety feature.

Brushes having sets of insecticide containing bristles containing the following insecticide combinations can also be used: 25% propoxur (both sets of bristles): 25% phosmer (both sets): 15% amitraz/25% lindane; 15% amitraz/25% propoxur; 15% amitraz/25% phosmet.

Accordingly, the invention also provides an article for grooming and controlling ectoparasites on an animal which includes a hand-grippable portion and a plurality of teeth or bristles of plastics material attached to the hand-grippable portion, with at last some of the teeth or bristles being flexible and containing at least one insecticide therein, the insecticide being capable of blooming from the plastics material onto the outer surfaces of the teeth of bristles are a relatively slow rate when the article is not in use and at a relatively fast rate in use when the bristles are flexed so that an insecticidally effective amount of insecticide is thereby applied to an animal being groomed.

The insecticide containing bristles may contain from 5 to 50% by mass insecticide, more preferably from 10 to 40%, still more preferably from 15 to 30% insecticide.

We claim:

1. An article for grooming and controlling ectoparasites on an animal which includes a hand-grippable portion and a plurality of teeth or bristles of plastics material attached to the hand-grippable portion, with at least some of the teeth or bristles being flexible and containing at least one insecticide moulded therein, the insecticide being capable of blooming from the plastics material onto the outer surfaces of the teeth or bristles at a relatively slow rate when the article is not in use and at a relatively fast rate in use when the bristles are flexed so that an insecticidally effective amount of insecticide is thereby applied to an animal being groomed.

2. An article for grooming and controlling ectoparasites on an animal, which is in the shape of a brush and which includes a hand-grippable portion; a plurality of teeth or bristles of plastics material attached to the hand-grippable portion, with at least some of the teeth or bristles being flexible and containing at least one insecticide moulded therein, and the insecticide being capable of blooming from the plastics material onto the outer surface of the teeth or bristles at a relatively slow rate when the article is not in use and at a relatively fast rate in use when the bristles are flexed so that an insecticidally effective amount of insecticide is thereby applied to an animal being groomed; and, in addition to the bristles of the insecticide-containing plastics matrial, also bristles which do not contain insecticide, with the insecticide containing bristles being softer than the non-insecticide-containing bristles.

3. An article for grooming and controlling ectoparasites on an animal, which is in the shape of a brush and which includes a hand-grippable portion, a plurality of teeth or bristles of plastics material attached to the hand-grippable portion, with at least some of the teeth or bristles being flexible and containing at least one insecticide moulded therein, and the insecticide being capable of blooming from the plastics material onto the outer surfaces of the teeth of bristles at a relatively slow rate when the article is not in use and at a relatively fast rate in use when the bristles are flexed so that an insecticidally effective amount of insecticide is thereby applied to an animal being groomed; at least two replaceable portions having only insecticide-containing bristles, the insecticide of the bristles of the one portion being different from that of the bristles of the other portion, and at least one further portion having non-insecticide-containing bristles.

* * * * *